United States Patent [19]

Millet et al.

[11] Patent Number: 4,537,782

[45] Date of Patent: Aug. 27, 1985

[54] EMULSIFYING SYSTEM BASED ON A FATTY ACID OR A PROTEIN CONDENSATE, A POLYOXYETHYLENATED STEROL AND A PHOSPHATIDE, AND A COSMETIC OR PHARMACEUTICAL COMPOSITION CONTAINING THE SAME

[75] Inventors: Catherine Millet, Paris; Jean-Claude Ser, Chevilly Larue; Quang L. N'Guyen, Antony, all of France

[73] Assignee: Societe Anonyme dite: L'Oreal, Paris, France

[21] Appl. No.: 459,496

[22] Filed: Jan. 20, 1983

[30] Foreign Application Priority Data

Jan. 28, 1982 [FR] France ................. 82 01329

[51] Int. Cl.$^3$ ............ A61K 7/021; A61K 7/42; A61K 31/685; A61K 47/00
[52] U.S. Cl. ..................... 514/774; 252/312; 424/DIG. 4; 424/59; 424/63; 424/68; 514/78; 514/784; 514/801
[58] Field of Search .......... 424/59, 365, 359, 358, 424/199; 252/312

[56] References Cited

PUBLICATIONS

Scafide et al., Cosmetics & Toiletries, 4/1980, pp. 65, 66, 69 to 72.
Proserpio et al., Cosmetics & Toiletries, 4/1980, vol. 95, pp. 81 to 85.
Kass, cosmetics & Toiletries, 4/1980, vol. 95, pp. 101, 106-108, 110-114, 116, 124 and 126.

*Primary Examiner*—Dale R. Ore
*Attorney, Agent, or Firm*—Cushman, Darby & Cushman

[57] ABSTRACT

An emulsifying system for use in the production of cosmetic or pharmaceutical compositions in the form of an emulsoid or gel comprises (i) at least one fatty acid having from 8 to 22 carbon atoms or a protein condensate of a fatty acid having from 8 to 40 carbon atoms and a polypeptide of animal origin, (ii) a polyoxyethylenated sterol and (iii) a phosphatide.

15 Claims, No Drawings

EMULSIFYING SYSTEM BASED ON A FATTY ACID OR A PROTEIN CONDENSATE, A POLYOXYETHYLENATED STEROL AND A PHOSPHATIDE, AND A COSMETIC OR PHARMACEUTICAL COMPOSITION CONTAINING THE SAME

The present invention relates to a new emulsifying system comprising (1) a fatty acid or a protein condensate, (2) a polyoxyethylenated sterol and (3) a phosphatide, said system providing an emulsoid or a gel.

The protein condensate employed in the present invention can be obtained from a fatty acid and collagen polypeptide. Such a condensate has previously been described and recommended as a co-emulsifying agent in emulsions of the water-in-oil or oil-in-water type. A phosphatide, such as egg lecithin or soy lecithin, as well as polyoxyethylenated sterols also possess emulsifying properties principally for emulsions of the oil-in-water type. However, these materials generally are not considered as principal emulsifying agents.

The "emulsoids" of the present invention are emulsions wherein the dispersing phase is a liquid and wherein the size of the particles contained therein is less than one micron.

This type of emulsion is particularly difficult to obtain using known emulsifying agents or using certain emulsifying systems constituted by a principal emulsifying agent and one or more co-emulsifying agents.

Gels are generally obtained either by using a gelling agent or by using an emulsifying agent or an emulsifying system. However, in this latter instance, an acceptable gel structure can only be obtained by using a relatively large amount of an emulsifying agent or an emulsifying system which renders the resulting gel particularly aggressive toward the skin.

It has now been noted that by using the emulsifying system of the present invention and by using this system in certain defined amounts, it is possible to obtain emulsoids as well as gels exhibiting a quite acceptable cosmetic appearance, great stability over prolonged periods of time, and having essentially no aggressiveness toward the skin.

Moreover, it has been established through the use of the emulsifying system of the present invention, cosmetic compositions can be obtained which exhibit a fineness incomparably superior to that of known water-in-oil or oil-in-water type emulsions.

The present invention thus relates to a new emulsifying system, the said system comprising:

(i) at least one fatty acid having 8 to 22 carbon atoms or at least one protein condensate of a fatty acid having 8 to 40 and a polypeptide of animal origin, (ii) a polyoxyethylenated sterol and (iii) a phosphatide.

Numerous tests which have been carried out have in effect shown that this combination of components is indispensible to the production of compositions which are indefinitely stable over time and which retain their fineness and their good cosmetic properties, such as their consistency and their good spreadability on the skin.

According to the present invention the emulsifying system preferably comprises (i) 5 to 60%, and more preferably 25 to 45%, of at least one fatty acid or a protein condensate, (ii) 5 to 45%, and more preferably 15 to 40%, of a polyoxyethylenated sterol, and (iii) 15 to 90%, and more preferably 20 to 60%, of a phosphatide.

The fatty acid component of the emulsifying system preferably has from 12 to 18 carbon atoms and can be saturated or unsaturated, branched or not, and can have one or more hydroxy functions.

Representative fatty acids include undecylenic acid, lauric acid, myristic acid, palmitic acid, stearic acid, isostearic acid, oleic acid, hydroxyoleic acid and linoleic acid.

The protein condensate useful in the present invention results, for example, from a reaction of the Schotten Baumann type between a polypeptide and a fatty acid in the form of its chloride (see A. Scafidi et al, Cosmetics and Toiletries, 1980, vol. 95, No. 4, p. 65).

Representative polypeptides capable of yielding these condensates of the present invention include, for instance, those derived from collagen or gelatin having a molecular weight between 200 and 20,000 and preferably lower than 10,000.

Representative fatty acids usefully employed to produce these protein condensates include, for instance, myristic acid, palmitic acid, stearic acid, isostearic acid, as well as the fatty acids of copra. According to the present invention these protein condensates can also be used in the form of their salts of a mineral or organic base and principally the salts of potassium hydroxide or triethanolamine.

According to a preferred embodiment of the present invention a liposoluble condensate of isostearic acid and a collagen polypeptide sold under the tradename of "CROTEIN IP" by Croda is used.

The polyoxyethylenated sterol is, preferably, a sterol polyoxyethylenated with 12 to 40 moles of ethylene oxide, and more preferably cholesterol oxyethylenated with 24 moles of ethylene oxides, such as that sold under the tradename "Solulan C-24" by Amerchol.

Also, in accordance with the invention polyoxyethylenated phytosterols and principally polyoxyethylenated stigmasterol, polyoxyethylenated sitosterol or polyoxyethylenated campesterol can be employed.

The phosphatide component of the emulsifying system of the present invention can be of animal or vegetable origin and is, principally, egg lecithin, soy lecithin, colza lecithin or turnsole lecithin. More preferably it is a derivative of egg lecithin such as diamidoester of phosphatidylcholine (lecithin amide-DEA, according to the CTFA—Cosmetic Toiletery Fragrance Association—Dictionary) or a complex of soy phospholipids sold under the tradename "EPIKURON 100 P" by Lucas Meyer Co.

The present invention also relates to, as a new industrial product, a cosmetic or pharmaceutical composition in the form of an emulsoid or a gel which is obtained using the emulsifying system of the present invention.

The concentration of the emulsifying system, as defined above, relative to the total weight of the cosmetic or pharmaceutical composition, is generally between 0.5 and 35 weight percent, the oil phase between 2 to 60 weight percent and the aqeuous phase between 30 and 97 weight percent.

When the composition of the present invention is provided in the form of an emulsoid, the concentration of the emulsifying system is between 2 and 15 weight percent, preferably between 5 and 13 weight percent; the oil phase, between 5 and 38 weight percent, preferably between 12 and 35 weight percent; and the aqueous phase, between 47 and 90 weight percent, preferably between 50 and 80 weight percent.

When the composition of the present invention is provided in the form of a gel, which can be a vibrating or swinging gel, the concentration of the emulsifying system is preferably between 15 and 30 weight percent; the oil phase, between 15 and 50 weight percent, preferably between 20 and 45 weight percent; and the aqueous phase, between 30 and 70 weight percent.

Representative oils usefully employed in the present invention to provide the oil phase include such products as: animal oils, including horse oil, hog oil and lanolin; vegetable oils, such as sweet almond oil, avocado oil, ricin oil, olive oil, grape seed oil, poppy oil, colza oil, peanut oil, corn oil, hazelnut oil, jojoba oil, safflower oil and wheat germ oil; hydrocarbon oils, such as paraffin oil, purcellin oil, perhydrosqualene and solutions of microcrystalline wax in oils; mineral oils and principally oils having an initial distillation point at atmospheric pressure of about 250° C. and a final distillation point in the order of 410° C.; and silicon oils soluble in other oils.

There can also be employed certain synthetic products such as, for example, esters and principally isopropyl palmitate, isopropyl myristate, butyl myristate, cetyl myristate, hexadecyl stearate and ethyl palmitate, as well as the triglycerides of octanoic and decanoic acids and cetyl ricinoleate.

The oil phase can also contain certain waxes and principally carnauba wax, beeswax, ozokerite or candellila wax.

The composition according to the present invention can also contain other components such as preservatives, antioxidants, perfumes, dyes, sun screen agents, pigments, humectants and charges such as talc, nylon powder, silk powder, starch powder or polyethylene powder and the like.

These cosmetic compositions can be provided in the form of hydrating creams as for example sun creams, face creams, body or hand creams or under the form of hydrating cheek rouge or complexion foundations.

When it is desired to obtain compositions for treatment of the skin, it is possible to include therein certain active substances such as agents to combat acne, anti-inflammatory agents, antibiotics, keratolytic agents, vitamins, astringents, anti-fungus agents or vasoconstrictor agents.

The following non-limiting examples are given to illustrate the present invention:

EXAMPLE 1

Protective cream for the skin provided in the form of an emulsoid

| Emulsifying system: | |
| --- | --- |
| Diamidoester of phosphatidylcholine - 7.5 g (50%) | } 15 g |
| Crotein IP - 4.5 g (30%) | |
| Solulan C24 - 3 g (20%) | |
| Petrolatum oil | 30 g |
| Isopropyl palmitate | 5 g |
| Preservative, sufficient amount | |
| Perfume, sufficient amount | |
| Water, sufficient amount for | 100 g |

EXAMPLE 2

Hydrating nightcream in the form of an emulsoid

| Emulsifying system: | |
| --- | --- |
| Diamidoester of phosphatidylcholine - 5.4 g (34%) | } 15.9 g |
| Crotein IP - 5.9 g (37%) | |
| Solulan C24 - 4.6 g (29%) | |
| Petrolatum oil | 18 g |
| Sweet almond oil | 6 g |
| Glycerine | 3 g |
| Perfume, sufficient amount | |
| Preservative, sufficient amount | |
| Sterile, demineralized water, sufficient amount for | 100 g |

EXAMPLE 3

Nourishing gel

| Emulsifying system: | |
| --- | --- |
| Diamidoester of phosphatidylcholine - 4.6 g (28.7%) | } 16 g |
| Crotein IP - 6 g (37.6%) | |
| Solulan C24 - 5.4 g (33.7%) | |
| Petrolatum oil | 12 g |
| Volatile silicone oil | 12 g |
| Perfume, sufficient amount | |
| Methyl parahydroxybenzoate | 0.3 g |
| Dye, sufficient amount | |
| Water, sufficient amount for | 100 g |

EXAMPLE 4

Transparent complexion foundation in the form of an emulsoid

| Emulsifying system: | |
| --- | --- |
| Soy lecithin (EPIKURON 100P) - 4.6 g (28.7%) | } 16 g |
| Solulan C24 - 5.4 g (33.7%) | |
| Crotein IP - 6 g (37.6%) | |
| Petrolatum oil | 12 g |
| Volatile silicone oil | 12 g |
| Methyl p-hydroxybenzoate | 0.3 g |
| Perfume, sufficient amount | |
| Dye, sufficient amount to color the composition | |
| Water, sufficient amount for | 100 g |

EXAMPLE 5

Nourishing gel

| Emulsifying system: | |
| --- | --- |
| Diamidoester of phosphatidylcholine - 6.9 g (28.7%) | } 24 g |
| Solulan C24 - 8.1 g (33.8%) | |
| Crotein IP - 9 g (37.5%) | |
| Petrolatum oil | 24 g |
| Volatile silicone oil | 12 g |
| Methyl p-hydroxybenzoate | 0.3 g |
| Perfume, sufficient amount | |
| Dye, sufficient amount to color the composition | |
| Water, sufficient amount for | 100 g |

EXAMPLE 6

Vibrating/Swinging Gel

| Emulsifying system: | |
| --- | --- |
| Diamidoester of phosphatidylcholine - 5.12 g (32%) | } 16 g |
| Isostearic acid - 5.44 g (34%) | |
| Solulan C24 - 5.44 g (34%) | |

-continued

| | |
|---|---|
| Petrolatum oil | 12 g |
| Volatile silicone oil | 12 g |
| Preservative, sufficient amount | |
| Perfume, sufficient amount | |
| Water, sufficient amount for | 100 g |

EXAMPLE 7

Day cream for dry skin in the form of an emulsoid

| | |
|---|---|
| Emulsifying system: | |
| Soy lecithin - 4.32 g (36%) | |
| Oleic acid - 3.6 g (30%) | 12 g |
| Solulan C24 - 4.08 g (34%) | |
| Petrolatum oil | 15 g |
| Turnsole oil | 8 g |
| Natural collagen, 0.3% solution in water | 10 g |
| Preservative, sufficient amount | |
| Perfume, sufficient amount | |
| Antioxidant, sufficient amount | |
| Water, sufficient amount for | 100 g |

EXAMPLE 8

Milk for oily skin having a tendency to acne, in the form of a microemulsion

| | |
|---|---|
| Emulsifying system: | |
| Diamidoester of phosphatidylcholine - 3.2 g (40%) | |
| Undecylenic acid - 3.2 g (40%) | 8 g |
| Solulan C24 - 1.6 g (20%) | |
| Petrolatum oil | 8 g |
| Isopropyl myristate | 4 g |
| S—carboxymethyl cysteine | 2 g |
| Preservative, sufficient amount | |
| Perfume, sufficient amount | |
| Antioxidant, sufficient amount | |
| Water, sufficient amount for | 100 g |

What is claimed is:

1. A emulsifying system to produce an emulsoid or gel comprising
   (i) 5 to 60 weight percent of at least one fatty acid having 8–22 carbon atoms or a protein condensate of a fatty acid having 8–40 carbon atoms and a polypeptide of animal origin,
   (ii) 5 to 45 weight percent of sterol polyoxyethylenated with 12–40 moles of ethylene oxide, and
   (iii) 15 to 90 weight percent of a phosphatide.

2. The emulsifying system of claim 1 wherein (i) is present in an amount of 25 to 45 weight percent, (ii) is present in an amount of 15 to 40 weight percent, and (iii) is present in an amount of 20 to 60 weight percent.

3. The emulsifying system of claim 1 wherein said fatty acid has 12–18 carbon atoms and is selected from the group consisting of undecylenic acid, lauric acid, myristic acid, palmitic acid, stearic acid, isostearic acid, oleic acid, hydroxyoleic acid and linoleic acid.

4. The emulsifying system of claim 1 wherein said polypeptide of animal origin is a derivative of collagen or gelatin having a molecular weight between 200 and 20,000.

5. The emulsifying system of claim 4 wherein said collagen or gelatin derivative has a molecular weight lower than 10,000.

6. The emulsifying system of claim 1 wherein the fatty acid of the protein condensate is selected from the group consisting of myristic acid, palmitic acid, stearic acid, isostearic acid and fatty acids of copra.

7. The emulsifying system of claim 1 wherein said protein condensate is in the form of a salt of a mineral or organic base.

8. The emulsifying system of claim 7 wherein the mineral base is potassium hydroxide.

9. The emulsifying system of claim 7 wherein the organic base is triethanolamine.

10. The emulsifying system of claim 1 wherein said polyoxyethylenated sterol is cholesterol oxyethylenated with 24 moles of ethylene oxide.

11. The emulsifying system of claim 1 wherein said phosphatide is a lecithin of vegetable or animal origin.

12. The emulsifying system of claim 11 wherein said lecithin is egg lecithin, soy lecithin, colza lecithin, turnsole lecithin or diamidoester of phosphatidylcholine.

13. A composition in the form of an emulsoid or gel comprising from 30 to 97 weight percent aqueous phase, from 2 to 60 weight percent oil phase and from 0.5 to 35 weight percent of the emulsifying system of claim 1.

14. A composition in the form of an emulsoid comprising from 47 to 90 weight percent aqueous phase, from 5 to 38 weight percent oil phase and from 2 to 15 weight percent of the emulsifying system of claim 1.

15. A composition in the form of a gel comprising from 30 to 70 weight percent aqueous phase, from 15 to 50 weight percent oil phase and from 15 to 30 weight percent of the emulsifying system of claim 1.

* * * * *